United States Patent
Horn

[11] Patent Number: 6,125,645
[45] Date of Patent: Oct. 3, 2000

[54] MOISTURE REMOVAL PHASE SHIFT PERSONAL COOLING GARMENT

[76] Inventor: Stephen T. Horn, 1661 James Wharf Rd., White Stone, Va. 22578

[21] Appl. No.: 09/017,341

[22] Filed: Feb. 2, 1998

Related U.S. Application Data

[60] Provisional application No. 60/049,749, Jun. 12, 1997.

[51] Int. Cl.[7] ..................... F25D 23/12
[52] U.S. Cl. ............. 62/259.3; 2/DIG. 1; 2/458
[58] Field of Search ............ 62/4, 259.3, 530, 62/457.2; 2/904, DIG. 1, DIG. 5, 458

[56] References Cited

U.S. PATENT DOCUMENTS

| | | |
|---|---|---|
| 3,429,138 | 2/1969 | Goldmerstein ............ 62/259.3 |
| 3,710,395 | 1/1973 | Spano et al. ............ 2/78 |
| 4,856,294 | 8/1989 | Scaringe et al. ............ 62/259.3 |
| 5,123,411 | 6/1992 | Noziri ............ 128/403 |
| 5,217,408 | 6/1993 | Kaine ............ 454/338 |
| 5,289,695 | 3/1994 | Parrish et al. ............ 62/259.3 |
| 5,415,222 | 5/1995 | Colvin et al. ............ 165/46 |
| 5,524,293 | 6/1996 | Kung ............ 2/102 |

*Primary Examiner*—William Doerrler

[57] ABSTRACT

The present invention provides a body cooling garment to easily and effectively protect the human body in hot conditions. By suspending in vapor contact a cold surface with channels in it's surface; moisture is evaporated from the body, condensed on the cold surface, and the body shielded from environmental heat. The condensed moisture is channeled from the garment.

13 Claims, 2 Drawing Sheets

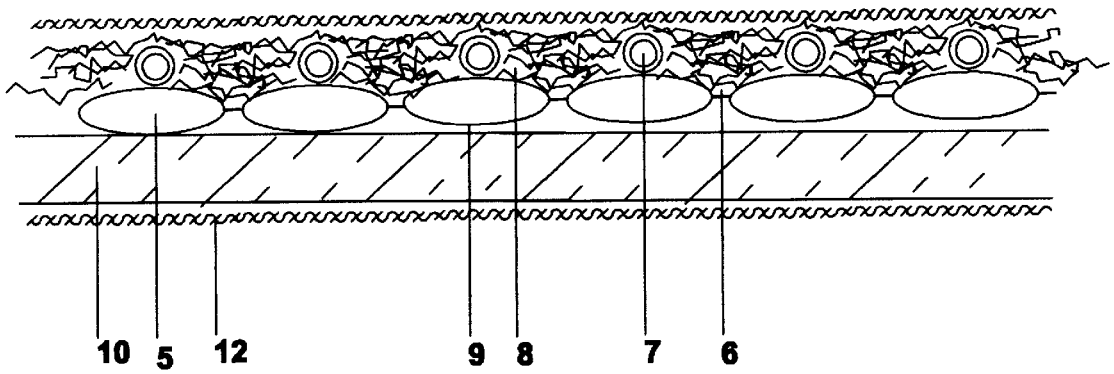
Fig. 2 Cross Section of Vest
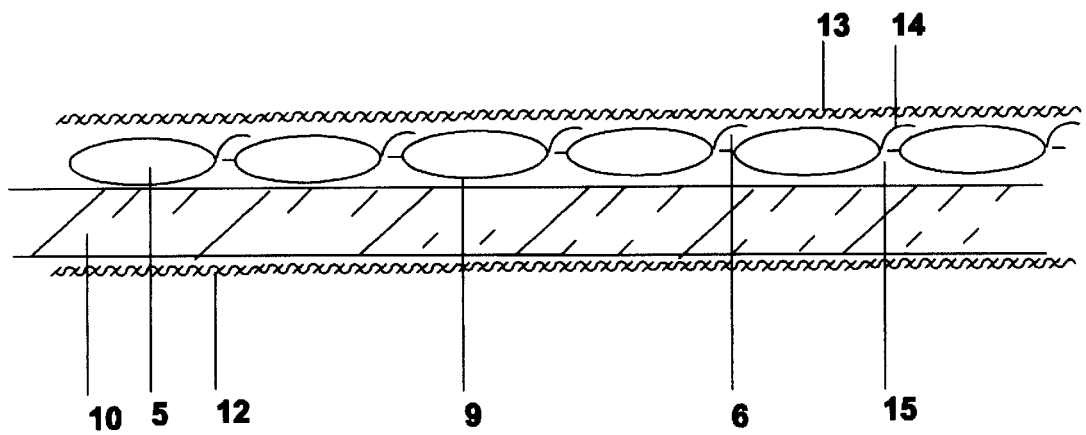
Fig.3 Cross Section of Vest
showing perferred embodiment(s)

MOISTURE REMOVAL PHASE SHIFT PERSONAL COOLING GARMENT

CROSS REFERENCE

A provisional patent application was filed on Jun. 12, 1997 the application Ser. No. was 60/049,749 the title was Personal Dehumidification Equipment.

FIELD OF THE INVENTION

The present invention relates to body garments capable of cooling the human body. This invention cools the body by surrounding it with a dry and cold environment and shielding it from outside heat. The dry environment within the garment allows evaporative cooling of the body. The body is also cooled by the cooling of the air immediately next to the body by the absorption of heat by a phase shift of a material. The phase shift material is used to dry the immediate environment around the body.

DESCRIPTION OF THE PRIOR ART

Body garments for the purpose of cooling appear in the patent record taking many shapes and forms. However, most of these patents regard body garments that cool through a closed circulation system of a cool liquid through a piping network incorporated into a garment or through the specially constructed garment itself having its own circulatory network. Another focus of the prior art concerns cooling apparatus that cool through evaporative means. These devices are open systems, as opposed to the closed circulation systems mentioned above, that release cool air or vapor onto and over an individuals body to cool through evaporative means. Another patent uses the phase shift of a material in a vest to cool a person but makes no reference to the removal of moisture as a method of cooling by increasing the evaporation of moisture from the wearer or a means of keeping a person comfortable. The present invention works in a different fashion than these above mentioned patented inventions. It keeps the body comfortable by absorbing heat directly from the body and by removing moisture away from the immediate environment around the body and condensing it on a cold surface. Thus reducing the relative humidity next to the body and increasing the evaporative cooling of the body and finally shielding the body from environmental heat. Experiments done by the inventor show that the transfer of body heat to a heat sink is more efficient and comfortable if the heat sink is used to reduce the humidity of immediate environment around the body and encourage the phase shift cooling that occurs when perspiration evaporates; rather than trying to absorb heat directly by placing the cold surface directly next to the body. This is because blood flow varies relative to the surface of the body and heat is tolerated better by some parts of the body than other parts. The body compensates by sweating more in some places than others (arm pits) and effects pilo erections of surface hair as well as contracts capillaries near the skin to keep other places warmer. Typically when a cooling vest that uses a cold surface placed next to the skin is used several things occur. First evaporation of moisture is prevented due to a high humidity immediately established above the skin Second if the cold surface is to be effective it must be colder than usual for the skin as usually vests cover only a small portion of the body. This causes constriction of small capillaries below the surface of the skin and the contraction of muscles raising small hairs on the skin (goose bumps). Thus one system on the body fights the method of direct cooling the body by an application of a cold surface as found in circulated water systems or systems with cold packs of frozen chemicals. Finally different parts of the body maintain different temperatures and the body so regulates. No cold surface system can practically compensate for this as different activities require different temperatures. The human body is designed to be surrounded by different temperature air and can compensate for this if the humidity of this air is low enough. And in hot environments if the temperature of the air can be reduced. The application of a cold surface directly to the body is inefficient and uncomfortable.

The present invention uses a cold surface to condense moisture out of the immediate environment next to the body. The cold surface is provided by the frozen quilted outer part of the garment. Channels are then provided between the quilt packages to remove the condensed moisture from the vest. The person is cool and dry.

For argumentative purposes the prior art is presented as follows. U.S. Pat. No. 3,507,321, issued to James R. Palma on Apr. 21, 1970, discloses clothing for cooling and heating the body. Palra's clothing affects the human body from the neck down by strategically locating heating coils and cooling conduits through the clothing. Temperature sensors are also incorporated into the clothing for accurate, electrical temperature control of the clothing. Moisture control is not considered.

U.S. Pat. No. 3,570,264, issued to Daniel L. Curtis on Mar. 16, 1971, discloses an evaporant cooling system comprising a light weight garment having a plurality of tubes connected in a parallel arrangement within the garment for the purposes of cooling the individual wearing same. This invention includes an inlet and an outlet manifold for circulating a liquid water-ammonia solution from a storage tank through the tubes. An exhaust port is also seen in fluid communication with the tubing for allowing the expended evaporant, the ammonia, to leave the system and further cool the individual. This is a cold surface system which cannot compensate for the bodies needs.

U.S. Pat. No. 3,610,323, issued to Dan E. Troyer on Oct. 5, 1971, also discloses an evaporative cooling garment to be worn by an individual This garment is seen as a vest-like coat having a plurality of passageways incorporated therein to create a coat from these side-by-side passageways. These passageways are also seen as having a plurality of openings thereon. When used, the Troyer coat is supplied from a reservoir with a quantity of liquid coolant comprising a water and refrigerant, preferably Freon, through an inlet valve. As the body is cooled the refrigerant evaporates, leaves the system, and is replaced from the reservoir until the [such] refrigerant has been depleted. No consideration is made for the condensing of moisture from the body is made.

U.S. Pat. No. 3,744,053, issued to Eugene K. Parker on Jul. 10, 1973, discloses liquid loop garments for heating and cooling the body of and individual. This system is a closed system, releasing no liquid or gas for either heating or cooling purposes. Parker's garments are constructed of two, liquid impervious, materials layers having insulation as well as other materials attached thereto. This again is a cold surface system which cannot compensate for the needs of the body.

Jumping ahead to U.S. Pat. No. 4,949,375, issued to Robert L. Nathans on Dec. 25, 1990, we see a mat utilizing the same type of closed system for circulating a fluid for cooling purposes that was disclosed in the Parker patent.

U.S. Pat. No. 4,998,415, issued to John D. Larsen on Mar. 12, 1991, discloses a body cooling apparatus including a tubing system for circulating a fluid that is moved not only through the tubing within the apparatus but through a compressor and a condenser in order to remove heat away from the body of an individual wearing the apparatus. Larsen's apparatus also includes a head cooling apparatus integrally connecting to the tubing of the main, body supported, apparatus for cooling the head of an individual. This once again is a cold surface cooling system that cannot compensate for the needs of the body.

U.S. Pat. No. 5,289,695, issued to Parrish and Scaringe on Mar. 1, 1994 discloses a device for adsorbing water with a desiccant. Desiccants such as calcium chloride are mentioned. The exothermic heat generated by the hydration of this desiccant is blocked from the body by an open cell foam layer. Thinsulate by 3M could be used to help insulate along with the open cell foam. A molecular sieve is mentioned as well as an adsorbent or absorbent material. The desiccant can be sealed in a plastic bag which can be opened to initiate adsorption. Valves and pumping of fluids from the desiccant are mentioned. The use of a cold surface to reduce the humidity of the immediate environment is not mentioned.

U.S. Pat. No. 4,964,282, issued to Christopher S. Wagner on Oct. 23, 1990, discloses a detachable bulletproof vest air conditioning apparatus. Wagner's apparatus comprises a piping system that connects to a pre-cooled air source and ducts and channels the air into the interior of the vest, between the vest and the individual, to cool the wearer of said vest.

U.S. Pat. No. 5,146,625, issued to Sandra L. Steele and Harry W. Nettleton on Sep. 15, 1992, discloses a vest with clothe pockets that contain a phase shift material. No provision is made for the removal of moisture. No provision is made for providing channels to drain the condensed moisture from the vest. No provision is provided for forced air.

U.S. Pat. No. 5,289,695, issued to Clyde F. Parrish and Rpbert P. Scaringe on Mar. 1, 1994, discloses a vest with a desiccant pad to absorb moisture and a foam to transport moisture to the pad. No provision is made to condense the moisture or channel it out of the garment. Rather the moisture is chemically absorbed. This patent fails to teach that with a cold surface; a chemical desiccant is not necessary to remove moisture, if the moisture can be channeled in some way from the vest.

U.S. Pat. No. 5,072,455, issued to Thomas A. St. Ours on Dec. 17, 1991, discloses multiple pocketed vest with coolant packs. No provision is made for the removal of moisture. No provision is made for wicking the moisture to the cold packs nor is any provision made to channel the moisture out of the vest. The use of forced air is not considered.

U.S. Pat. No. 4,170,793, issued to Scott T. O'Brien on Oct. 16 1979, discloses a vest with a cotton inner lining which wicks moisture from the individual and allows for evaporation of moisture. No provision is made for actively absorbing the heat of the individual through a heat sink nor is there any provision for condensing the moisture of the individual so that it can be transported from the vest. No provision is made for the removal of moisture with forced air.

U.S. Pat. No. 5,415,222, issued to David P. Colvin and Yvonne G. Bryant on Mar. 1, 1994, discloses a vest which has pouches of a coolant which does not cover the entire surface of the vest but rather allows evaporative cooling to occur where the pouches do not touch the wearer. No provision is made for the condensation and removal of moisture from the vest. Moisture is not condensed and channeled out in liquid form but rather is allowed to passively evaporate through pours in the vest. There are no channels for the transport of moisture or provision for the wicking of moisture to the channels.

Exothermal Tech makes a vest which has a phase change material designed to phase shift around 70F in a sectioned plastic bag which is encased in a cloth shell. The sections are large and run diagonally no provision is made to wick moisture to these plastic bags. The close and immediate contact of the heat sink to the skin of the wearer prevents the removal of moisture from the body. The relatively high temperature of the phase shift material is insufficient to condense the moisture. There are no vertical channels in the sides of the vest to transport the condensed moisture. There is no provision for the removal of moisture with forced air.

SUMMARY OF THE INVENTION

Accordingly, it is a principal object of the invention to provide a convenient and inexpensive body cooling garment that does not require the use of expensive refrigerants yet still is capable of cooling the body. The present invention is a vest or garment to be worn either under protective clothing or alone and to protect a person from environmental heat. The vest is designed to absorb humidity from the body and condense it on a cold surface. It uses a phase shift material such as melting ice as a heat sink. This heat sink also limits environmental heat from the outside environment from effecting the body. The garment absorbs and transport the moisture given off from the body through initial capillary action in conjunction with vapor transfer which is effected by the reduction of humidity immediately next to the body or with the additional use of forced air. The vest after a few minutes reduces the relative humidity immediately next to the wearer to the point where perspiration is rapidly evaporated into the dry immediate atmosphere next to the body and condensed on the cold surface in the vest.

One embodiment of the invention is lined with connected plastic packages of a phase shift material (frozen water) with a material which would provide an air space from the cold surface and allow moisture to condense on the package. The term wicking material is often used when referring to the transfer of water vapor through a material especially when referring to garments. Patagonia brand polyester pile jackets are said to wick moisture to the outside of the jacket. Travelsmith brand bras made of polyester materials are said to be moisture wicking when it could be understood that they are vapor permeable. The material used to provide the air space between the skin and the cold surface would be of this type. It would not be adsorbent. The moisture condensed on these cold packs is then conveyed down formed channels between the cold packs and then dripped from the vest. The width and spacing of the vertical channels is determined by the rate of condensation and the surface tension of the perspiration and the size of droplets formed. The material, between the cold packs and the wearer, is a synthetic low absorption material such as polyester batting or Nomex™ batting held in place by a fabric screen, but would not be limited to such. The batting keeps the frozen water packages suspended off the surface of the body to allow condensation to form droplets on the cold surface and flow to the channels. Any material other than batting that would keep the cold surface in the immediate close proximity to the body would do. The body is cooled by passive absorption of heat by the cold dry air surrounding the body and by the phase shift of perspiration to a vapor encouraged by the dryness of the immediate environment around the body.

The inventor conducted an experiment where a double layer of cotton material was soaked in water to represent the skin of a hot individual this was laid on a flat marble slab to maintain a constant temperature. On top of this was placed 3/16 in. layer of polyester batting. Then two electrical sensors, each constructed of a pair of 1/16 in stainless steel rods held 1/16 in apart were laid on the polyester batting. One electrical sensor was wrapped in wet cotton and the other in dry cotton. Current flow could be measured in the electrical sensor (electric hygrometer) wrapped in the wet cotton but none in the dry. (The wet cotton was soaked and then wrung out.) Next another layer of 3/16 in polyester batting was placed over the electrical sensors. This polyester spacer permits the transfer of water vapor yet does not readily transfer liquid. Finally a large flat bag of frozen water sealed in mylar was laid on top of all. This containment structure of frozen water (ice) was quilted by sealing 1/4 in. wide seams every 1 1/2 inch to form 1 1/2 inch squares with channels between them; like a quilt. So we have the skin represented by the soaked cotton and then a double layer of polyester with electrical sensors in between and a cold channeled surface (heat absorbing means). Intuitively we would expect a current flow between the rods of the electrical sensor wrapped in wet cotton to remain the same and the sensor wrapped in dry cotton to become wet and show a flow of electricity. What in fact happens is the dry cotton electrical sensor initially gains a small flow of current but then drops rapidly so that no current flow is detected. The wet cotton electrical sensor rather than having the current flow remain constant shows almost an immediate drop in conductivity. This drop in current flow across the wet cotton continues to drop to the point where no current can be detected after about an hour. Counter to what is expected the wet cotton on the two stainless rods is rapidly drying out. This drying is happening even though the soaking wet cotton on the marble slab is still very wet. The quilted bag of frozen water is now wet. If this set up is tilted the water condensed on the quilted cold surface begins to run down the channels and out of the apparatus. By completely covering the soaking wet cotton with the quilted cold surface suspended above it by the polyester batting air flow from the outside is reduced or practically eliminated and a dry arid and cool environment is created next to the soaking wet cotton surface representing the skin. This surface begins to cool by two processes i.e. evaporative cooling and the absorption of heat by the cold air next to it. As a control experiment, if the soaked cotton surface representing the skin is left dry instead of soaking it with water no condensation can be found on the cold surface next to the polyester. It remains dry although the other side where it is exposed to air in the room condensed moisture. This control experiment confirms the condensed moisture in the first experiment, is moisture that evaporated from the wet cotton simulating the skin. As to why the electrical sensor wrapped in dry cotton begins to conduct electricity and then stops is believed to be due to initial wicking from the soaking wet cotton surface until evaporation exceeds the wicking in the polyester. The inventor does not wish to be held to this explanation.

Polyester used in this apparatus and in the invention does not really wick as cotton does, however it does permit water vapor to transfer and limits condensed moisture transfer. The inventor refers to this material as a vapor wicking medium as opposed to a capillary action wicking medium. Other materials beside polyester would be suitable, in fact most man made fibers will work, while untreated cotton does not work. Untreated cotton just becomes saturated with water and directly conduct heat to the cold surface. A garment incorrectly using a material with the water absorbing characteristics of untreated cotton, will make the wearer feel clammy and wet.

The cooling vest works in a like manner to the experiment described above. Its effectiveness in cooling an individual is more than the amount of calories transferred by simple conduction to the frozen water in the vest. The utilization of the cooling effect of the phase change of perspiration into a vapor by the reduction of absolute humidity next to the skin and the drop of water vapor pressure allowing more perspiration to be evaporated significantly enhances the effective cooling and comfort of the vest. This is so because the water (perspiration) is continually channeled from the vest. This efficiency is further enhanced by the physiological demands of the body. The body self regulates the evaporation of perspiration in different parts of the body according to need. It does so by among others varying the amount of sweat and controlling the air flow immediately next to the skin by the selective erection of hair on the skin and the contraction of capillaries under the skin.

The construction of the cold surface to condense the moisture on is important. It must be channeled to allow the condensed moisture to leave the vest. If the vest is to be used horizontally a vapor permeable but water proof membrane must seal FIG. 3, 13 the channels from the polyester. Examples of this is Gortex™ or the house wrap Tyvek ™. These allow water vapor to pass but prevent the back flow of water. This set up is used when gravity alone will not be enough to channel condensed water from the vest. The quilting in any shape square, round, irregular, of the cold pack is an excellent method of providing channels in the vest for moisture removal. By making the cold surface of 1 1/2 inch squares with a 1/4 channel allows flexibility in the vest. Also by having the squares connected it seals the immediate environment next to the skin from out side air allowing the air to be dried and cooled. If cold packs are merely attached end to end on only one or two sides as in the Steele vest U.S. Pat. 5,146,625, a pocket must be sewn into a cooling vest or garment to hold each row of cold packs, however if the cold packs are quilted then the vest becomes easier to make. Also water does not collect from condensation and wet the wearer at the seam of the vest pocket. Further the necessity to make sewn pockets necessitates that the size of the cool pack be larger than otherwise or the seams from the pockets will take up a large portion of the vest. This creates another problem in that the large cold pack which is most often filled with a liquid or powder settles to the bottom and unnecessarily thickens and more importantly adds weight to the vest. An experiment with a 4 in by 4 in polyethylene baggy of water will demonstrate that to cover a 4 in sq. surface requires a bag filled almost two inches thick. However, if a 4 in by 4 in quilted bag, if quilted with three bags across and three down, the same surface can be accommodated with a thickness of much less than one inch and consequently less than half the weight. Each bag in tension supports the other bag.

A lip forming a gutter FIG. 3, 14 is incorporated in another embodiment on some of the horizontal channels of the cold surface. A drain hole FIG. 3, 15 is provided to convey moisture out the drain hole to the outside of the vest. The addition of an up turned edge of plastic sealed to a horizontal channel would form a gutter at the bottom of a row. It is used to channel condensed moisture through a small hole in the channel to the out side of the cold pack.

In situations where a large individual or individuals who perspire a lot are very active it is possible that the evaporation of moisture in the immediate dry cold environment next to the skin could be overwhelmed. It would be essential to prevent the saturation of the vest and direct thermal contact between the skin and the cold pack surface. In these cases the vest would be equipped with a perforated tubing network to pump in forced air from a belt mounted blower or otherwise. Vests require a minimum of 30 psi to operate effectively. Channels already formed in the vest could used to deliver the air where a downward flow would increase the flow of condensed moisture down the quilted cold surface and out of the vest. The forced air would be either user controlled or automatic using an electrical sensor to determine the absolute humidity in the immediate environment next to the skin and compare this to the temperature and absolute humidity outside the vest or garment. The object being to prevent saturation of the vest and a chilling of the wearer. Thermal contact with the wearer would shorten the length or time the cold surface would be effective.

Experiments done by the inventor has shown that the effective cooling time of the vest is strongly effected by outside environmental heat melting (phase shift) the cold surface. In a very hot environment it would seem that putting a heavy coat over a cooling vest or garment of the type above would be counter productive. However this not the case. Providing insulation to the outside of the garment significantly increases the length of time the cold surface can effectively condense moisture and cool the body. The best insulation by weight is an aerogel silica foam as manufactured by Aspen Systems Incorporated, Marlboro, Mass. Also by providing a reflective layer such as mylar is also effective. When price is considered, the most effective outside insulation is polyfoam a polyester closed cell foam used in packageing.

BRIEF DESCRIPTION OF THE DRAWINGS

Drawings

DETAILED DESCRIPTION OF THE PREFERRED EMBODIMENT(s)

Figure 1:
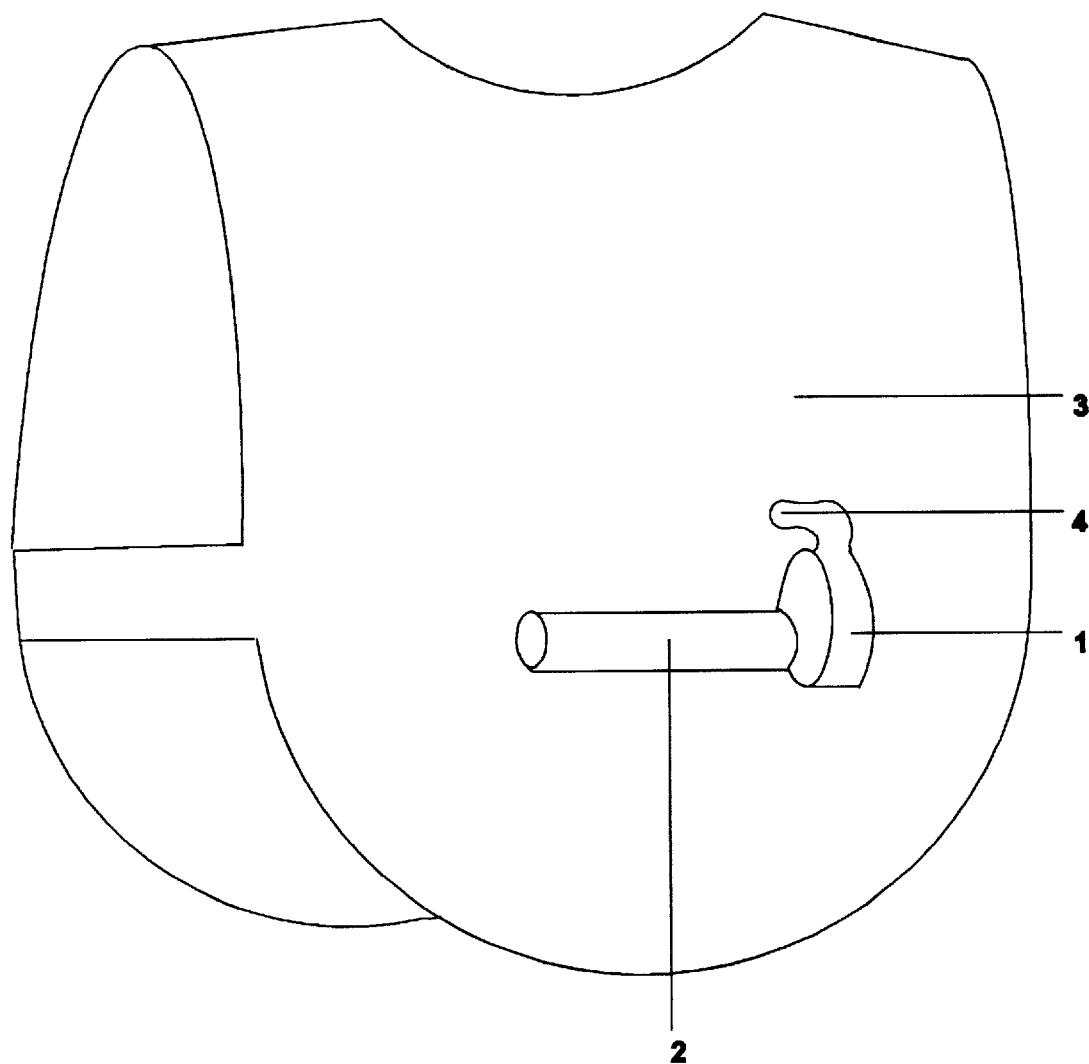
FIG. 1
1. Blower
2. Battery
3. Garment
4. Connection of blower to tubing network under vest
   FIG. 2 Cross Section of Vest
5. Phase shift material package (ice mat) (cold surface)
6. Moisture channel
7. Air tube
8. Vapor wicking medium (pellon)
9. Infrared reflective surface
10. Insulation to protect from environmental heat (polyfoam)
11. Inner garment shell (textiline)
12. Outer garment shell (textiline)
    FIG. 3 Cross Section of Vest showing Preferred Embodiment(s)
5. Phase shift material package (ice mat) (cold surface)
6. Moisture channel
9. Infrared reflective surface
10. Insulation to protect from environmental heat
12. Outer garment shell
13. Vapor permeable but water proof membrane (Gortex™)
14. Lip to form gutter
15. Hole Similar reference characters denote corresponding features consistently throughout the attached drawings. Round brackets are to help identify and to clarify but are not intended to limit the materials used.

The present invention relates to independent and portable body garments that cool the body. The present invention is distinct from those already patented in that provides for the removal of moisture from the body both to keep the person comfortable and to cool the body. The invention allows the wearer to remain both cool and dry in very hot conditions. The vest is also designed to use a cold pack 5 with a surface designed to reflect infrared spectrum light 9. A mylar material such as used in "space blankets" is presently used with the reflective side out and a non-reflective side next to the body thus heat from the body is not reflected back to it but is absorbed. The cold pack (packaged phase shift material) 5 is further designed to be sectioned into rectangular sections which are attached on multiple sides to be quilt like in construction. Presently a sheet of approximately 1½ inch squares is used with approximately ¼ in seam between packages top, bottom, and sides. Five packages thus measuring a little less than 10 inches across; the spacing of the vertical channels should allow transport of condensation (perspiration) horizontally with out dripping. This also eliminates the necessity of multiple fabric pockets in the vest. Vests with cold packs attached only end to end require a fabric pocket to hold the packs. The tracks between the quilted cold packets form a channel 6 for the removal of condensed humidity. Moisture condenses on the pack and moves across it and down between the packs uninterrupted by any cloth pockets and ultimately out the bottom of the vest. The moisture is transported from the body to the cold packs by a material 8 that allows vapor transport of water. Both polyester batting and Nomex™ batting if treated work well. This spacer for the removal of moisture is very important. In other vests the condensed moisture that condenses on the packet collects at the bottom of the fabric pocket or transfers back through the vest and wets the wearer. This wetness inhibits evaporative cooling of the wearer due the reduction of the surface area of the skin. Surface irregularities and hair follicles are covered with rounded beads of moisture.

The quilted cold pack 5 in this vest is made flexible by the addition of multiple channels on the pack on more than one axis. It also limits the phase change material from collecting at the bottom and ballooning the packet after it returns to a liquid state. The sectioning allows a thinner vest to be made as smaller cooling packs are possible due to the limitation of the seam width of individual pockets in other vests. If individual pockets were sewn into the vest, there would be many fabric seams where there would be no phase change material to absorb the heat. The bottom of each small phase change material pack supports the other without a sewn pocket. The quilted cooling pack also allows a staggering of seams of phase change material when two layers are used, hence providing continuous coverage of the body. This construction also allows a much lighter garment to be made as the elimination of usually fabric pockets allows smaller packets to be used of the phase change material. Larger packets are used in present vests due to the fact that the phase change material such as water sags as a liquid and must be of a certain size to allow adequate coverage of a body and allow for a minimum number of sewn pockets in a vest. By using a quilted pattern of at least three rows by three columns each package of phase change material supports the other and a vest can be made thinner. The vest uses five by ten package cold packs to allow the formation of channels to convey downward moisture. On legs or arms an even smaller package quilt would be used to further reduce the thickness and weight.

The construction procedure presently used for a vest is as follows where textiline™ is a mesh like fabric as used on trampolines, polyfoam™ is a packing material made of close celled polyethylene, ice mat is the quilted cold surface and pellon™ is a polyester batting material.

1. Cut out pattern of textiline fabric for both inside FIG. 2, 11 and outside 12 of vest shell. Cut 2 in. velcro pieces to length if velcro is to be used for fastening other wise disregard velcro. Two strips will be sewn across the front of the vest, loop out.
2. Completely sew bottom front velcro on the outer textiline 11 only.
3. Sew top front velcro only on seam farthest the head hole. We will sew the bottom seam of the top velcro later to hold the insulation and 1 inch velcro sticky type in place.
4. Sew back pieces of 2 in velcro on and roll the loose ends to prevent the from catching on everything.
5. Lay large textiline vest shell pieces 11 and 12 together and sew hole for head.
6. Cut out from insulation pattern two pieces of pellon insulation 8.
7. Install pellon 8 between two pieces of textiline 1 land 12 by pulling outside layer of vest through the head hole cut out in the pellon 8.
8. Cut out from ⅛ poly foam 10 two pieces using the insulation pattern.
9. Install poly foam 10 on top of pellon 8 under outer layer of textiline 12. You will have a sandwich of textiline with two layers of pellon and two layers of poly foam later separated with a layer of ice mat (cold surface) shiny side facing the polyfoam.
10. Along the bottom seam line of the top velcro strip in the front, place two 1 inch velcro sticky tape strips inside hook down between the pellon 8 and the polyfoam 10. Place them at least four inches from the edge. Should no 2 in velcro be used made this seam half way up front and back of vest. Sticky tape velcro should go perpendicular to the seam and half above the seam and half below. They will be used to stick the ice mat 5 in place in the vest. We will peel back the sticky tape and stick the ice mat 5 (cold surface) firmly to the sticky side of the velcro. Other wise the ice mat 5 can be held alone between textiline 11 and 12 the stick tape velcro can also be omitted.
11. On the back of the vest there is a seam line as well do the same again with the 1 in velcro. The hook side of the sticky tape velcro if used should face the pellon 8.
12. Cut the ice mat5(cold surface) pieces for the front and back of the vest to allow for neck hole.
13. Install ice mat 5 between the poly foam 11 and the pellon 8. The pellon 8 being the inside of the vest the poly foam 11 insulating the outside. Peel back the outside of the one inch velcro exposing the sticky back and firmly anchor the blue side of the ice mat. Won't stick if mat is cold or wet. The silver mylar side should shine outward to reflect heat trying to get through the vest . If dividing seams are sewn in the front and back of the fabric 11 and 12; then four ice mats two front and two back must be installed.
14. Bind outside of vest using care not to puncture the ice mat(s) 5.
15. The vest is completed other garments for legs etc. are made simular.

Another embodiment uses to enhance the removal of moisture from the garment the use of forced air is used. Experimentation has shown that a minimum of 30 psi is needed to effectively remove moisture from a vest of this type. The forced air is delivered through perforated tubes 7 in the vest in a network to distribute the air; although the channels between the phase change material could be used as a vector for the air flow. The air is supplied independently from a compressor or a belt mounted blower 1. The direction of the air flow would be downward to encourage the flow of moisture from the cold pack.

FIG. 3 shows two other distinct embodiments. First is a Gortex™ film described as vapor permeable but water proof membrane 13 preventing back flow of condensed water from the cold surface 5. This is also sealed, in another embodiment, to lips 14 to positively remove moisture through hole or moisture transfer means 15 to the outside of the garment. (cotton could be used to wick moisture through the hole but in this particular embodiment would not be necessary) Also shown in FIG. 3 is the gutter arrangement on the horizontal rows of the cold surface 5. The lip 14 traps water as it condenses and runs down 5 and instead of allowing it to drip from the bottom of the vest; it moves the condensed water to the outside of the vest where it would be used again in evaporative cooling. In this case the outside insulation 10 would be a vapor wicking medium such as pellon but not limited to such. Experiments show that the additional phase shift of moisture on the insulating surfaces of the outside of the garment significantly lengthens the cooling time of the garment.

Although the invention has been described and illustrated in detail, it is to be understood the same is by way of illustration and example and is not to be taken by way of limitation. The spirit and scope of the present invention are to be limited only by the terms of the appended claims.

I claim:

1. A method of cooling the body of a wearer of a cooling garment, said method comprised of the following steps:
1. supporting a hydrophobic spacer means next to said body,
    a) supporting a cold surface next to said hydrophobic spacer means,
    b) evaporating perspiration from said body into vapor phase water,
    c) transferring said vapor phase water through said hydrophobic spacer means,
    d) condensing said vapor phase water into liquid phase water on said cold surface, thus cooling said body.

2. The cooling garment of claim 1 wherein said cold surface is cooled by endothermic chemical reaction.

3. The cooling garment of claim 1 wherein said cold surface is cooled by frozen chemical.

4. The cooling garment of claim 1 wherein said hydrophobic spacer means is synthetic fiber batting.

5. A garment for cooling the body of a wearer fashioned of layered components into a generally rectangular garment having opposite end edges and opposite side edges, said garment having a head opening in a generally central location for accommodating head and neck of said wearer, front and rear panels, defined by said head opening, for overlaying chest and back of said wearer respectively, said garment having an inside surface being the surface closest to the body of said wearer, said front and rear panels comprising layers, presented here in an order starting with the claimed layer closest to said inside surface as follows: a spacer layer of a vapor permeable hydrophobic material on the inside of a heat absorbing layer having a temperature below the dew point of water with a substantially unrestricted vapor travel between the wearer and the heat absorbing layer.

6. The cooling garment of claim 5 wherein said heat adsorbing layer is comprised of multiple quilted sections wherein the space between the said multiple quilted sections forms a substantially vertical channel.

7. The cooling garment of claim 5 wherein heat adsorbing layer is cooled by a endothermic chemical reaction.

8. The cooling garment of claim 5 wherein heat adsorbing layer comprises a sealed container containing a frozen chemical.

9. The cooling garment of claim 5 wherein said vapor permeable hydrophobic material is synthetic fiber batting.

10. The cooling garment of claim 5 wherein a vapor permeable but waterproof membrane is placed next to said heat absorbing layer.

11. The cooling garment of claim 5 wherein an insulating layer is placed on the outside of said heat adsorbing layer.

12. The cooling garment of claim 1 wherein said cold surface is comprised of multiple quilted sections wherein the spaces between the said multiple quilted sections forms substantially vertical channels.

13. The process of claim 1 with the added step of draining said liquid water off of said cold surface and away form said body.

* * * * *